United States Patent
Young

(10) Patent No.: US 10,520,510 B2
(45) Date of Patent: Dec. 31, 2019

(54) METHODS FOR DETECTING AND QUANTIFYING NON-POLAR ANALYTES WITH HIGH SENSITIVITY

(71) Applicant: Waters Technologies Corporation, Milford, MA (US)

(72) Inventor: Michael S. Young, Bellingham, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 141 days.

(21) Appl. No.: 15/349,384

(22) Filed: Nov. 11, 2016

(65) Prior Publication Data

US 2017/0138953 A1    May 18, 2017

Related U.S. Application Data

(60) Provisional application No. 62/255,058, filed on Nov. 13, 2015.

(51) Int. Cl.
*G01N 33/64* (2006.01)
*G01N 30/72* (2006.01)
(Continued)

(52) U.S. Cl.
CPC ............ *G01N 33/64* (2013.01); *B01D 15/26* (2013.01); *G01N 30/7233* (2013.01);
(Continued)

(58) Field of Classification Search
CPC ........ G01N 33/64; G01N 33/50; G01N 33/48; G01N 30/7233; G01N 30/72; G01N 30/62;
(Continued)

(56) References Cited

U.S. PATENT DOCUMENTS 8,507,844 B2    8/2013 Mazza
2016/0108038 A1*    4/2016 Alig .................... C07D 471/04
                                                    504/100

FOREIGN PATENT DOCUMENTS

WO    2001036067 A1    5/2001
WO    2003074145 A1    9/2003
WO    WO-2014195232 A1    12/2014

OTHER PUBLICATIONS

Chowdhury, M. Alamgir Zaman et al., Detection of the residues of nineteen pesticides in fresh vegetable samples using gas chromatographyemass spectrometry, Food Control, 34, 2013, 457-465. (Year: 2013).*

(Continued)

*Primary Examiner* — Christine T Mui
(74) *Attorney, Agent, or Firm* — Womble Bond Dickinson (US) LLP; Deborah M. Vernon

(57) ABSTRACT

The technology of the present application is directed to methods and kits for detecting and quantifying a non-polar analyte in a plant-derived sample. The technology uses a simple extraction, e.g., a liquid-liquid extraction (LLE) or solid-phase extraction (SPE), to enrich a sample for a non-polar analyte of interest and to remove contaminants. After the extraction and clean-up steps, liquid chromatography and mass spectrometry are used to detect the non-polar analyte. In one embodiment, acequinocyl and/or its derivatives is analyzed using liquid chromatography and tandem mass spectrometry (LC-MS/MS) and the improved LC-MS/MS conditions allows detection limits of acequinocyl and/or its derivatives of 50 ppb or less.

20 Claims, 4 Drawing Sheets

(51) Int. Cl.
  B01D 15/26 (2006.01)
  G01N 30/88 (2006.01)
  G01N 1/34 (2006.01)
  G01N 1/40 (2006.01)
  G01N 30/00 (2006.01)
  G01N 30/02 (2006.01)

(52) U.S. Cl.
  CPC .............. G01N 30/88 (2013.01); G01N 1/34 (2013.01); G01N 1/405 (2013.01); G01N 2001/4061 (2013.01); G01N 2030/009 (2013.01); G01N 2030/027 (2013.01); G01N 2430/10 (2013.01); G01N 2560/00 (2013.01)

(58) Field of Classification Search
  CPC ........ G01N 30/02; B01D 15/26; B01D 15/08; B01D 15/00
  USPC ...................................................... 436/128
  See application file for complete search history.

(56) References Cited

OTHER PUBLICATIONS

Merriam-Webster.com definition of 'extract', https://www.merriam-webster.com/dictionary/extract, obtained on Aug. 30, 2018, p. 1-20. (Year: 2018).*

Dankyi, Enock, et al, "Quantification of neonicotinoid insecticide residues in soils form cocoa plantations using a QuEChERS extraction procedure and LC-MS/MS", Science of the Total Environment, Elsevier, Amsterdam, NL, vol. 499, Sep. 6, 2014 (Sep. 6, 2014), pp. 276-283.

EPO Search Report, European Application No. 16198405.9, dated Mar. 17, 2017.

Korta E, et al; "Study of semi-automated solid-phased extraction for the determination of acaricide residues in honey by liquid chromatography", Journal of Chromatography A, Elsevier, Amserdam, NL, vol. 930, No. 1-2, Sep. 28, 2001 (Sep. 28, 2001). pp. 21-29.

Sukesh Narayan Sinha, et al; "Quantification of Organophosphate insecticides and herbicides in vegetable samples using the Quick Easy Cheap Effective Rugged and Safe (QuEChERS) method and a high-performance liquid chromatographyelectrospray ionisationmass spectrometry (LC-MS/MS) technique", Food Chemistry, Elseview LTD, NL, vol. 132, No. 3, Nov. 23, 2011 (Nov. 23, 2011), pp. 1574-1585.

"Method 1664, Revision B: n-Hexane Extractable Material (HEM; Oil and Grease) and Silica Gel Treated n-Hexane Extractable Material (SGT-HEM; Non-polar Material) by Extraction and Gravimetry." pp. 1-10. Cited as Reference D13 in the Notice of Opposition filed in European Application No. 16198405.9 dated Feb. 14, 2019.

"Supelco Bulletin 910: Guide to Solid Phase Extraction" pp. 1-12. Cited as Reference D8 in the Notice of Opposition filed in European Application No. 16198405.9 dated Feb. 14, 2019.

Castillo et al. "An evaluation method for determination of non-polar pesticide residues in animal fat samples by using dispersive solid-phase extraction clean-up and GC-MS." Anal. Bioanal. Chem. 400(2011): 1315-1328.

Chai et al. "Determination of Organochlorine Pesticides in Vegetables by Solid-Phase Extraction Cleanup and Gas Chromatography." Pertanika J. Sci. Technol. 11.2(2003): 249-259.

Communication of a Notice of Opposition filed in European Application No. 16198405.9 dated Feb. 14, 2019.

Davies et al. "Development of a Multiclass Cleanup Method Incorporating a Novel SPE Media for the Analysis of Mycotoxins in Grain Using LC-MS/MS." p. 1. Cited as Reference D1 in the Notice of Opposition filed in European Application No. 16198405.9 dated Feb. 14, 2019.

Majors. "Salting-out Liquid-Liquid Extraction (SALLE)." LCGC. 27.7(2009): 526-533.

Mills et al. "Rapid Method for Chlorinated Pesticide Residues in Nonfattty Foods." J. Assoc. Official Agric. Chemists. 46.2(1963): 186-191.

Notice of Opposition as filed in European Application No. 16198405.9 dated Feb. 8, 2019.

Response to Notice of Opposition as filed in European European Application No. 16198405.9 dated Jul. 1, 2019.

Schenck et al. "Determination of Pesticides in Food of Vegetal Origin." Analysis of Pesticides in Food and Environmental Samples. (2008): 151-176.

Wilkowska et al. "Determination of pesticide residues in food matrices using the QuEChERS methodology." Food Chem. 125(2011): 803-812.

Young et al. "Multi-Residue Pesticide Analysis in Chili Powder: Optimized Cleanup After QuEChERS Extraction for UPLC-MS/MS and GC-MS/MS Analysis." pp. 1-6. Cited as Reference D4 in the Notice of Opposition filed in European Application No. 16198405.9 dated Feb. 14, 2019.

Young et al. "Multi-Residue Pesticide Analysis in Ginseng Powder: Optimized Cleanup After QuEChERS Extraction for UPLC-MS/MS and GC-MS/MS Analysis." pp. 1-6. Cited as Reference D3 in the Notice of Opposition filed in European Application No. 16198405.9 dated Feb. 14, 2019.

Young et al. "Multi-Residue Pesticide Analysis in Tea: Optimized Cleanup After QuEChERS Extraction for UPLC-MS/MS and GC-MS/MS Analysis." pp. 1-8. Cited as Reference D2 in the Notice of Opposition filed in European Application No. 16198405.9 dated Feb. 14, 2019.

* cited by examiner

METHODS FOR DETECTING AND QUANTIFYING NON-POLAR ANALYTES WITH HIGH SENSITIVITY

RELATED APPLICATIONS

This application claims the benefit of U.S. Provisional Application No. 62/255,058, filed on Nov. 13, 2015, the entire contents of which are hereby incorporated herein by reference.

FIELD OF THE INVENTION

The present disclosure relates to methods for detecting non-polar analytes in plant-derived samples with high sensitivity, i.e., at low detection limits.

BACKGROUND OF THE INVENTION

Pesticide residue is often found on plants and food crops, and acceptable levels of such pesticide residue are often stipulated by regulatory bodies in many countries and in every state of the United States. Exemplary analytical methods currently used for detecting various pesticides in plant-derived samples at the regulatory limits specified by the states of Massachusetts (Mass.) and Nevada (Nev.) are illustrated in Table 1 below.

TABLE 1

Exemplary Analytical Methods for Detecting Pesticides

| Pesticide | Regulatory Limit (ppb) MA | Regulatory Limit (ppb) NV | Analytical Method |
|---|---|---|---|
| Abamectin | | 50 | LC/MS, Quechers |
| Acequinocyl | 20 | 4000 | LC/MS |
| Bifenazate | 20 | 15000 | LC/MS, Quechers |
| Bifenthrin | 20 | 50 | GC-MS, LC/MS, Quechers |
| Captan | | 50 | GC/MS, Quechers |
| Chlormequat chloride | 20 | | LC/MS, MeOH/H2O/FA |
| Cyfluthrin | 20 | 4000 | GC-MS, LC/MS, Quechers |
| Cypermethrin | | 50 | GC-MS, LC/MS, Quechers |
| Daminozide (Alar) | 20 | | LC/MS, MeOH/H2O/FA |
| Dimethomorph | | 60000 | LC/MS, GC/MS, Quechers |
| Etoxazole | 20 | 7000 | LC/MS, GC/MS, Quechers |
| Fenhexamid | | 30000 | LC/MS, Quechers |
| Fenoxycarb | 20 | | LC/MS, Quechers |
| Flonicamid | | 7000 | LC/MS, Quechers |
| Fludioxanil | | 20 | LC/MS, Quechers |
| Imazalil | 20 | | LC/MS, Quechers |
| Imidacloprid | | 50 | LC/MS, Quechers |
| Myclobutanil | 20 | 9000 | LC/MS, Quechers |
| Pentachloronitrobenzene | | 200 | GC/MS, Quechers |
| Paclobutrazol | 20 | | LC/MS, Quechers |
| Pyrethrins | 20 | 1000 | GC-MS, LC/MS, Quechers |
| Spinetoram | | 1700 | LC/MS, Quechers |
| Spinosad | 20 | 1700 | LC/MS, Quechers |
| Spiromesifen | | | LC/MS, GC/MS, Quechers |
| Spirotetramat | 20 | 10000 | LC/MS, Quechers |
| Thiamethoxam | | 20 | LC/MS, Quechers |
| Trifloxystrobin | 20 | 11000 | LC/MS, GC/MS, Quechers |

Quechers is an acronym that stands for Quick Easy Cheap Effective Rugged Safe and refers to a commonly used procedure for extracting analytes, e.g., pesticides, from plant-derived materials for subsequent analysis. The original Quechers method has been described in Anastassiades et al., *J. AOAC Int.* (2003), 86(2): 412-31, the entire contents of which are incorporated herein by reference. Quechers generally involves two steps: the first step is the production of a raw extract, while the second step is a clean-up step to remove various contaminants. The first step involves mixing with agitation a plant-derived sample with a solution comprising acetonitrile and various salts to produce the raw extract. The second step involves removing various contaminants, e.g., non-polar contaminants, from the raw extract by, e.g., solid phase extraction (SPE) to generate a solution containing the analyte of interest. The analyte of interest can then be subsequently detected and quantified by, e.g., gas chromatography and mass spectrometry (GC/MS) or liquid chromatography and mass spectrometry (LC/MS).

However, current analytical methods used for analyzing pesticide content, e.g., methods that utilize Quechers, are not suitable for detecting and analyzing certain non-polar analytes. An exemplary non-polar analyte is acequinocyl with the structure as shown below:

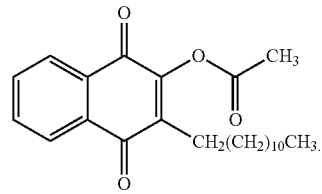

Acequinocyl is a pesticide found in cannabis, hops and other highly resinous dried commodities and is highly non-polar and practically insoluble in water. The clean-up step for removing non-polar contaminants used in the current analytical methods also removes non-polar analytes, such as acequinocyl, from the sample. This results in high levels of matrix interferences and leads to poor reproducibility and insufficient sensitivity of the non-polar analyte detection. Because the government-specified regulatory limits for non-polar analytes, e.g., acequinocyl present in cannabis for medicinal use, may be especially low, the current analytical methods are inadequate for ensuring that the regulatory limits are met. Furthermore, because it is difficult to achieve the required sensitivity of detection using the current analytical methods, an increased amount of sample, e.g., twice the amount, is needed for the analysis. As a result, costs for performing the analysis is overly expensive. Therefore, improved analytical methods providing both inexpensive and sensitive detection and quantification of non-polar analytes, e.g., acequinocyl, in plant-derived samples are needed.

SUMMARY OF THE INVENTION

Accordingly, in some embodiments, the present invention provides highly sensitive methods for detecting non-polar analytes, e.g., acequinocyl. The methods use a simple extraction, e.g., a liquid-liquid extraction (LLE) or solid-phase extraction (SPE) to enrich a sample for a non-polar analyte of interest and to remove contaminants. For example, the methods of the present invention substitute the second step of the Quechers methods with an LLE or an SPE to enrich for a non-polar analyte while also removing contaminants. After the extraction and clean-up steps, liquid chromatography and mass spectrometry are used to detect the non-polar analyte. In one embodiment, acequinocyl and/or its derivatives is analyzed using liquid chromatography and tandem mass spectrometry (LC-MS/MS) and the improved LC-MS/MS conditions, allowing to achieve detection limits of acequinocyl and/or its derivatives 50 ppb or less.

In some embodiments, the present invention provides a method for detecting and quantifying a non-polar analyte in a plant-derived sample, comprising (a) purifying the sample in a first purification step to obtain a first solution; and (b) purifying the first solution in a second purification step comprising extracting the first solution using a non-polar phase to obtain a second solution.

In some embodiments, the second solution comprises the non-polar analyte and the method results in detection of the non-polar analyte at a detection limit that is equal to or lower than a threshold detection limit.

In some aspects, the method of the invention further comprises (c) subjecting the second solution to an analysis by liquid chromatography (LC) followed by mass spectrometry (MS).

In some embodiments, the liquid chromatography is ultra high pressure liquid chromatography (UHPLC). In some embodiments, a mobile phase for said liquid chromatography comprises ammonium acetate. In some aspects, the mass spectrometry is tandem mass spectrometry (LC/MS/MS).

In some embodiments, the non-polar phase is a non-polar solid phase or a non-polar liquid phase. In some aspects, the liquid non-polar phase is a non-polar solvent, e.g., a non-polar solvent selected from the group consisting of pentane, hexane, cyclohexane, benzene, toluene, chloroform, diethyl ether and 1,4-dioxane. In one embodiment, the non-polar solvent is hexane. In another embodiment, the non-polar solid phase is a C18 phase.

In some embodiments, the first purification step comprises extraction with a solution comprising acetonitrile and at least one salt. In some embodiments, the at least one salt is selected from the group consisting of sodium chloride, magnesium sulfate, trisodium citrate dehydrate and disodium hydrogen citrate sesquihydrate.

In some aspects, the plant-derived sample comprises hops or cannabis.

In some aspects, the non-polar analyte is acequinocyl, an acequinocyl derivative or a combination thereof. In one embodiment, the acequinocyl derivative is acequinocyl-OH.

In some embodiments, the threshold detection limit is 1000 ppb or less, 100 ppb or less, 50 ppb or less, 10 ppb or less, or 1 ppb or less.

In some aspects, the present invention also provides a method for detecting and quantifying acenoquinocyl, an acequinocyl derivative or a combination thereof in a sample comprising cannabis, comprising: (a) purifying said sample in a first purification step to obtain a first solution; and (b) purifying the first solution in a second purification step comprising extracting the first solution using a hexane to obtain a second solution comprising acequinocyl.

In some embodiments, the second solution comprises acequinocyl and the method results in detection of acequinocyl at a detection limit of 50 ppb or less.

In some aspects, the method further comprises (c) subjecting the second solution to an analysis by liquid chromatography (LC) followed by mass spectrometry (MS). In some embodiments, the liquid chromatography is ultra high pressure liquid chromatography (UHPLC). In some embodiments, a mobile phase for the liquid chromatography comprises ammonium acetate. In some aspects, the mass spectrometry is tandem mass spectrometry (LC/MS/MS). In some embodiments, the LC/MS/MS comprises multiple reaction monitoring (MRM) using an ion selected from the group consisting of an ion having an M/Z of $343^+$, $385^+$ or $402^+$.

In some embodiments, the present invention also provides a kit for detecting and quantifying a non-polar analyte in a plant-derived sample at a detection limit that is equal to or lower than a threshold detection limit of 1000 ppb or less, comprising reagents necessary to purify a plant-derived sample in a first purification step to obtain a first solution; a non-polar phase; and instructions for use. In some aspects, the non-polar phase is a non-polar solid phase or a non-polar liquid phase. In some embodiments, the liquid non-polar phase is a non-polar solvent, e.g., a non-polar solvent is selected from the group consisting of pentane, hexane, cyclohexane, benzene, toluene, chloroform, diethyl ether and 1,4-dioxane. In some aspects, the non-polar solvent is hexane. In some embodiments, the non-polar solid phase is a C18 phase.

BRIEF DESCRIPTION OF THE DRAWINGS

The foregoing and other aspects provided by embodiments of the present technology will be more fully understood from the following description when read together with the accompanying drawings.

DETAILED DESCRIPTION OF THE INVENTION

Methods of the Invention

Figure 1:
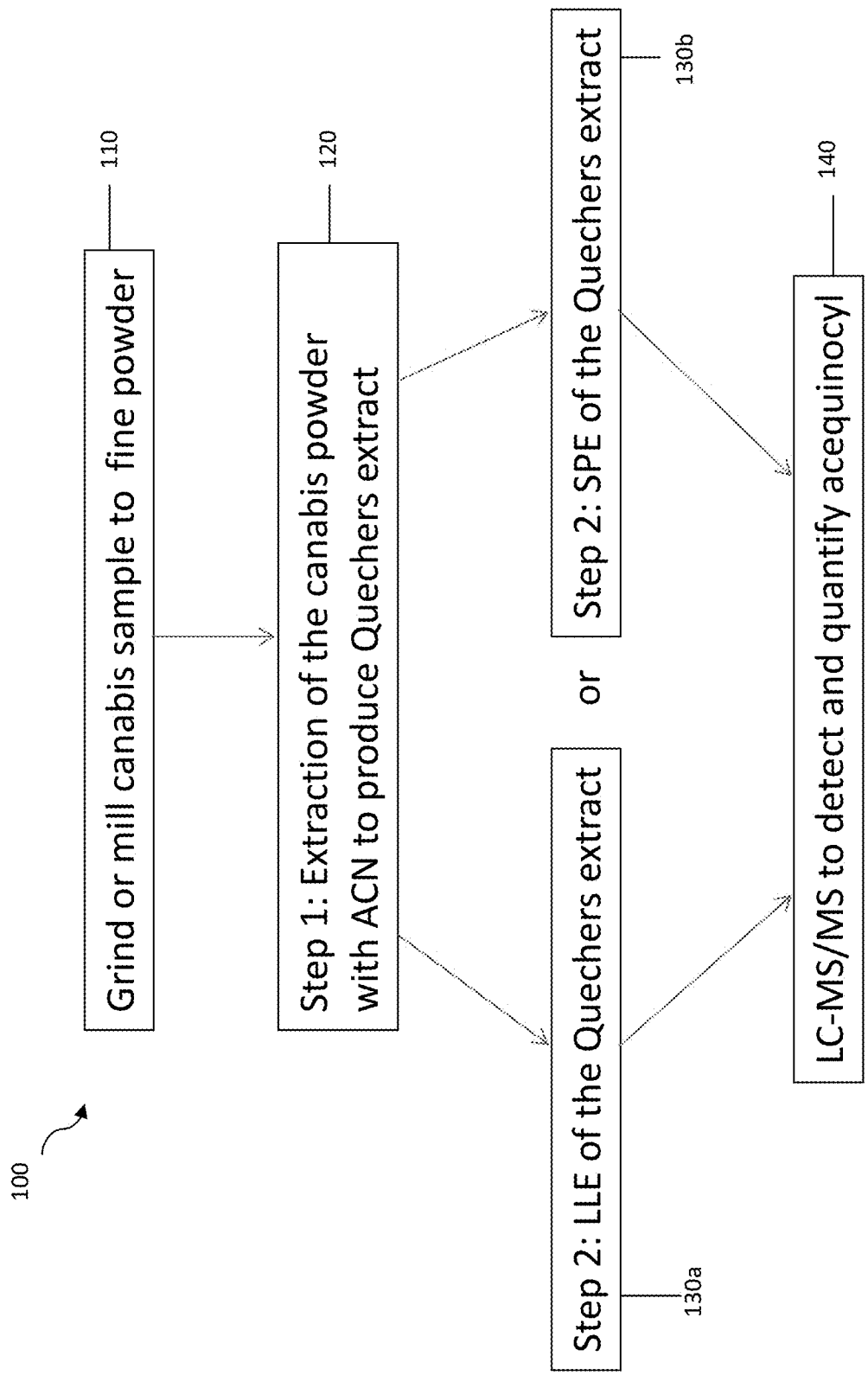
FIG. 1 is a flowchart illustrating a procedure for detecting and quantifying acequinocyl according to one embodiment of the invention.

In some embodiments, the present invention provides methods for detecting and quantifying a non-polar analyte in a plant derived sample. In one embodiment, the method of the invention comprises the following steps:

(a) purifying said sample in a first purification step to obtain a first solution; and (b) purifying said first solution in a second purification step comprising extracting said first solution using a non-polar phase to obtain a second solution.

In some embodiments, the second solution comprises the non-polar analyte and the method results in detection if this non-polar analyte at a detection limit that is equal or lower than a threshold detection limit.

The term "threshold detection limit", as used herein, refers to a target detection limit for a given non-polar analyte. In some embodiments, the threshold detection limit is the regulatory limit for a given non-polar analyte in a given country or a state of the United States. In some embodiments, the threshold limit may be 1000 ppb or less, 950 ppb or less, 900 ppb or less, 850 ppb or less, 800 ppb or less, 750 ppb or less, 700 ppb or less, 650 ppb or less, 600 ppb or less, 550 ppb or less, 500 ppb or less, 450 ppb or less, 400 ppb or less, 350 ppb or less, 300 ppb or less, 250 ppb or less, 200 ppb or less, 150 ppb or less, 100 ppb or less, 90 ppb or less, 80 ppb or less, 70 ppb or less, 60 ppb or less, 50 ppb or less, 40 ppb or less, 30 ppb or less, 20 ppb or less, 10 ppb or less, 9 ppb or less, 8 ppb or less, 7 ppb or less, 6 ppb or less, 5 ppb or less, 4 ppb or less, 3 ppb or less, 2 ppb or less or 1 ppb or less.

In a specific embodiment, the threshold detection limit for acequinocyl and/or its derivatives is the regulatory limit for acequinocyl in a given country or a state of the United States. In some embodiments, the threshold detection limit for acequinocyl is 50 ppb or less, 45 ppb or less, 40 ppb or less, 35 ppb or less, 30 ppb or less, 25 ppb or less, 20 ppb or less, 15 ppb or less, 10 ppb or less, 9 ppb or less, 8 ppb or less, 7 ppb or less, 6 ppb or less, 5 ppb or less, 4 ppb or less, 3 ppb or less, 2 ppb or less or 1 ppb or less.

In some embodiments, the method of the invention further comprises:

(c) subjecting the second solution to an analysis by liquid chromatography (LC) followed by mass spectrometry (MS). In certain embodiments, the mass spectrometry may be tandem mass spectrometry (LC-MS/MS).

The liquid chromatography may be, e.g., ultra high pressure liquid chromatography (UHPLC). The liquid chromatography may be performed using a mobile phase comprising an agent that facilitates subsequent detection of the non-polar analyte by mass spectrometry, e.g., tandem mass spectrometry. For example, when the non-polar analyte is acequinocyl and/or its derivatives, such as acequinocyl-OH, the mobile phase for the liquid chromatography may comprise an ammonium salt, e.g., ammonium acetate.

In some embodiments, step (b) of the method of the invention comprises extracting the first solution using a non-polar phase to obtain the second solution. The non-polar phase may be a non-polar liquid phase, e.g., a non-polar solvent, or a non-polar solid phase, e.g., a C18 solid phase. The non-polar solvent may be pentane, hexane, cyclohexane, benzene, toluene, chloroform, diethyl ether and 1,4-dioxane. In a specific embodiment, the non-polar solvent is hexane.

In some embodiments, when LLE using a non-polar liquid phase is used in the second purification step (b), the non-polar analyte is retained in the non-polar liquid phase. In such instances, the second solution is the non-polar liquid phase containing the non-polar analyte.

In some embodiments, when SPE is used in the second purification step (b), the non-polar analyte is initially retained on the solid phase, e.g., a C18 solid phase, and is then eluted from the solid phase in a separate elution step. In such instances, the second solution is the eluate from the solid phase containing the non-polar analyte.

In some embodiments, the first purification step (a) in the methods of the invention comprises producing a raw extract. For example, the first purification step (a) may comprise extracting a plant-derived sample with a solution that comprises acetonitrile (ACN) and at least one salt. In a specific embodiment, the at least one salt may be selected from the group consisting of sodium chloride, magnesium sulfate, trisodium citrate dehydrate and disodium hydrogen citrate sesquihydrate. In some embodiments, the first purification step is the first step of the Quechers procedure.

The plant-derived sample suitable for use in the methods of the present invention may be any plant-derived sample that may comprise a non-polar analyte, e.g., a non-polar pesticide. For example, the plant-derived sample may comprise hops or cannabis. The non-polar pesticide may be acequinocyl, an acequinocyl derivative, e.g., acequinocyl-OH, or a combination thereof.

In some embodiments, the present invention also provides a method for detecting and quantifying acenoquinocyl, an acequinocyl derivative or a combination thereof in a sample comprising cannabis. The method may comprise the following steps:

(a) purifying said sample in a first purification step to obtain a first solution; and (b) purifying said first solution in a second purification step comprising extracting said first solution using a hexane to obtain a second solution comprising acequinocyl, an acquinocyl derivative or a combination thereof.

In certain aspects, the second solution comprises acequinocyl, an acequinocyl derivative or a combination thereof, and the method results in detection of acequinocyl, an acequinocyl derivative or a combination thereof at a detection limit of 50 ppb or less, e.g., 45 ppb or less, 40 ppb or less, 35 ppb or less, 30 ppb or less, 25 ppb or less, 20 ppb or less, 15 ppb or less, 10 ppb or less, 9 ppb or less, 8 ppb or less, 7 ppb or less, 6 ppb or less, 5 ppb or less, 4 ppb or less, 3 ppb or less, 2 ppb or less or 1 ppb or less.

The method for detecting and quantifying acenoqunocyl, an acequinocyl derivative or a combination thereof in a sample comprising cannabis may further comprise:

(c) subjecting said second solution to an analysis by liquid chromatography (LC) followed by mass spectrometry (MS).

The liquid chromatography may be, e.g., ultra high pressure liquid chromatography (UHPLC). The mobile phase for the liquid chromatography may comprise an ammonium salt, e.g., ammonium acetate. It has been surprisingly discovered that the presence of ammonium salt, e.g., ammonium acetate, in the mobile phase during liquid chromatography in step (c), leads to formation of an ammonium adduct of acequinocyl. The ammonium adduct of acequinocyl produces a highly abundant and reproducible mass spectrometric peak at m/z 402 corresponding to $(M+NH_4)^+$. In the absence of ammonium salt, the peak corresponding to the protonated molecular ion for acequinocyl (m/z 385) is not reproducible. Accordingly, presence of an ammonium salt in the mobile phase allows a robust and reproducible detection and quantification of acequinocyl or its derivative and allows to lower the detection limit of the analytical method.

The tandem mass spectrometry analysis may comprise multiple reaction monitoring (MRM) using an ion selected from the group consisting of an ion having an M/Z of $343^+$, $385^+$ or $402^+$. In some embodiments, mass spectrometric transitions $402 \rightarrow 343$ and $402 \rightarrow 189$ may be monitored during the tandem mass spectrometry.

Kits of the Invention

The present invention also provides kits for detecting and quantifying a non-polar analyte in a plant-derived sample at a detection limit that is equal to or lower than a threshold detection limit of 1000 ppb or less. The kit may comprise reagents necessary to purify a plant-derived sample in a first purification step to obtain a first solution; a non-polar phase; and instructions for use.

The non-polar phase may be a non-polar solid phase, e.g., a C18 phase, or a non-polar liquid phase, e.g., a non-polar solvent. The non-polar solvent may be selected from the group consisting of pentane, hexane, cyclohexane, benzene, toluene, chloroform, diethyl ether and 1,4-dioxane. In a specific embodiment, the non-polar solvent is hexane.

EXEMPLIFICATION OF THE INVENTION

Example 1

Analysis of Acequinocyl in Cannabis

A procedure (100) for detecting and analyzing acequinocyl in cannabis is shown in FIG. 1. The purpose of Step 1 of the analysis is to obtain an acetonitrile (ACN) extract of cannabis or other dry commodity using a modified Quechers method. First, the cannabis sample was ground or milled to obtain a fine powder (110). A 1 gram portion of this prepared sample was transferred to a 50 mL polypropylene centrifuge tube along with 10 mL of pure water. The sample was vortexed or shaken for 30 seconds and allowed to equilibrate at room temperature for 30 minutes. Subsequently, 10 mL of ACN were added, and the sample was placed on a mechanical shaker for 30 minutes. Subsequently, 1 gram of trisodium citrate dihydrate, 0.5 grams of disodium hydrogen citrate sesquihydrate, 1 gram of sodium chloride and 4 grams of anhydrous magnesium sulfate were added to the sample to induce phase separation between the water and ACN. The sample was shaken vigorously for 2 minutes and then centrifuged (120). A 2 mL aliquot of the supernatant was used for the subsequent Step 2.

Step 2 of the analysis may be carried out using either LLE (130a) or SPE (130b). For LLE, a 2 mL aliquot of the Quechers extract obtained in Step 1 was transferred to a 15 mL centrifuge tube, combined with 4 mL of hexane, and the sample was shaken vigorously for 30 seconds. The tube was then centrifuged, and a 2 mL aliquot of the supernatant was taken. The aliquot was evaporated using a gentle nitrogen stream at 40° C., and was then reconstituted in 200 μL CAN (130a). For SPE, a 2 mL aliquot of the Quechers extract obtained in Step 1 was combined with 0.5 mL of water, and the mixture was loaded onto a tC18 Sep-Pak cartridge (500 mg), washed with 1 mL of ACN and then eluted with 3 mL of hexane. The eluate was evaporated using a gentle nitrogen stream at 40° C. and reconstituted in 200 μL acetonitrile (130b).

Step 3 of the analysis involved LC-MS/MS analysis using the improved conditions for high sensitivity of detection of acequinocyl (140). The analysis was performed using a Xevo TQD mass-spectrometer in positive electrospray mode. A 100×2.1 mm Acquity BEH C18 column was used for the analytical separation. The mobile phase was 92.5% methanol and 7.5% water with 10 mM ammonium acetate. This unique mobile phase composition, and, specifically, ammonium acetate present in the mobile phase, affords a reproducible and high-abundance ammonium adduct in the mass-spectrum for acequinocyl. In combination with the improved cleanup obtained in Step 2, this unique mass-spectral adduct allows for much lower detection limits compared with prior methods (140).

Figure 2:
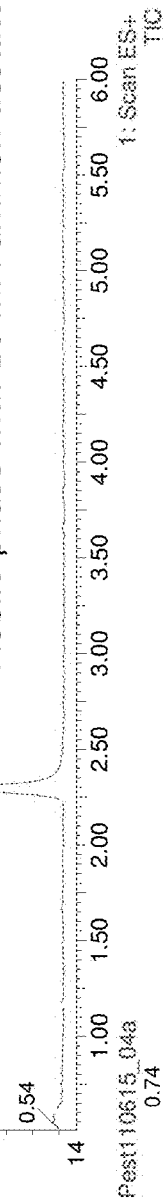
FIG. 2 is a panel showing total ion chromatogram (TIC) of the LLE purified Quechers extract of cannabis obtained using the mobile phase containing 10 mM ammonium acetate (top panel); mobile phase containing 0.1% formic acid (middle panel); and mobile phase without any additives (bottom panel).
Figure 2:
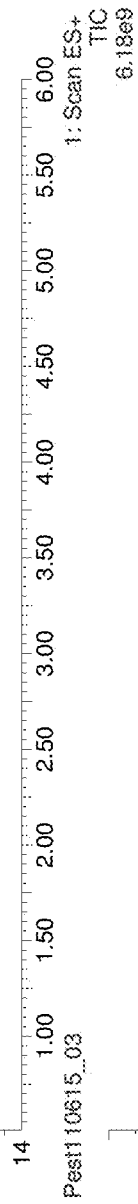
Figure 2:

FIG. 2 is a panel showing the total ion chromatogram (TIC) of the LLE purified Quechers extract of cannabis obtained using different mobile phases, such as the mobile phase containing 10 mM ammonium acetate (top panel); mobile phase containing 0.1% formic acid (middle panel); and mobile phase without any additives (bottom panel). FIG. 2 illustrates that the mobile phase containing 10 mM ammonium acetate produces the most robust and clean signal in the TIC. In contrast, the mobile phase containing 0.1% formic acid produces a less robust signal, and the mobile phase with no additives produces no signal at all.

Figure 3:
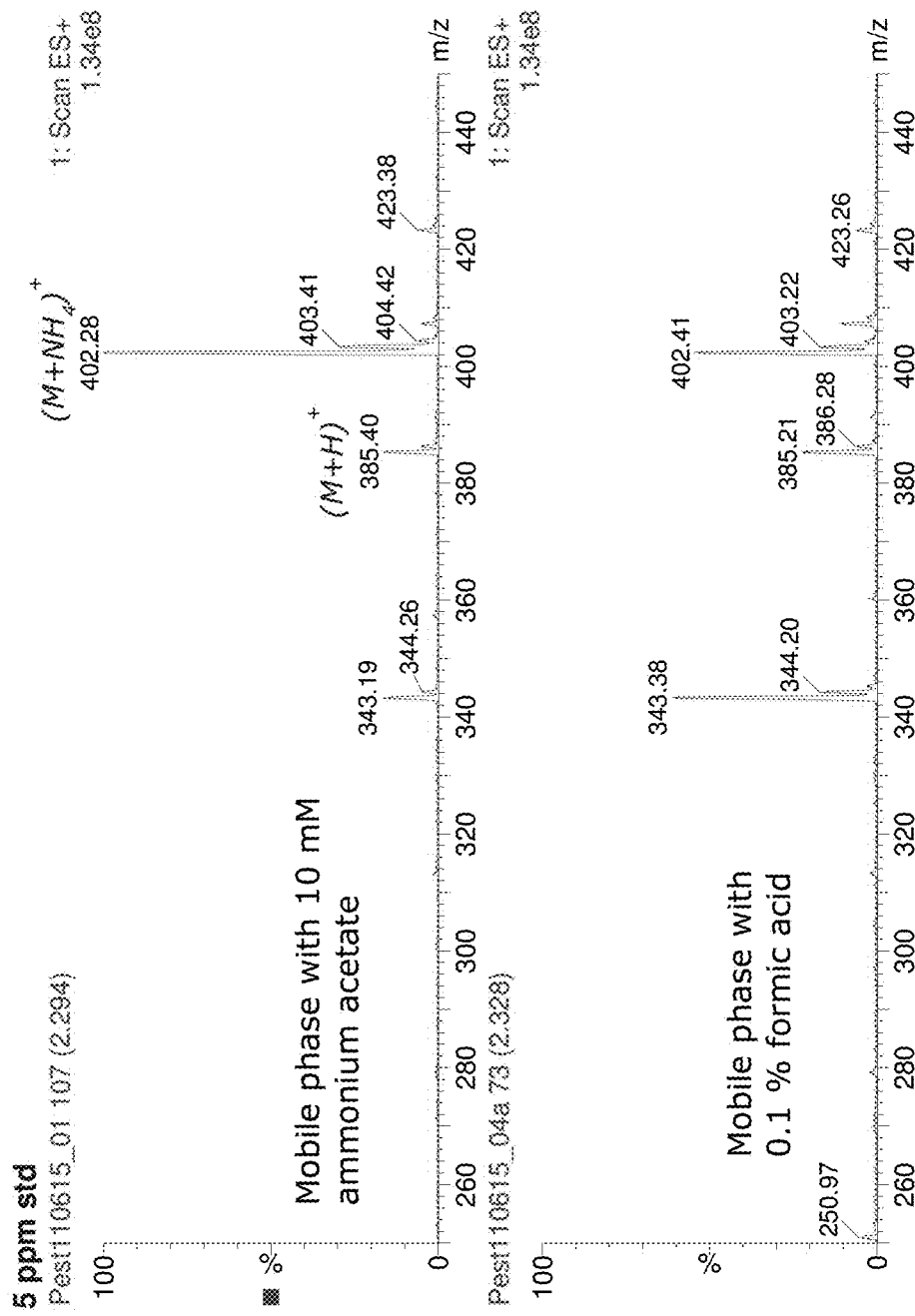
FIG. 3 is a panel showing mass spectra of the chromatographic peaks at 2.29 minutes and 2.33 that appear in the TICs shown in FIG. 1.

FIG. 3 is a panel showing mass spectra of the chromatographic peaks at 2.29 minutes and 2.33 in the TICs shown in FIG. 2. Specifically, the top panel of FIG. 3 is the mass spectrum of the peak at 2.29 minutes shown in the top panel of FIG. 2 when the mobile phase containing 10 mM ammonium acetate is used. The bottom panel of FIG. 3 is the mass spectrum of the peak at 2.33 minutes shown in the middle panel of FIG. 2 when the mobile phase containing 0.1% formic acid is used. FIG. 3 illustrates that when ammonium containing additive, such as ammonium acetate, is added to the mobile phase, the resulting ammoniated adduct of acequinocyl (corresponding to the peak at m/z 402.28) is readily detected in the mass spectrum because it has high abundance and is reproducible. In contrast, with no added ammonium, e.g., when the mobile phase containing 0.1% formic acid is used, variable adduct formation is observed and neither the ammoniated adduct, nor the protonated molecular ion of acequinocyl (m/z 385) is reproducible.

Figure 4:
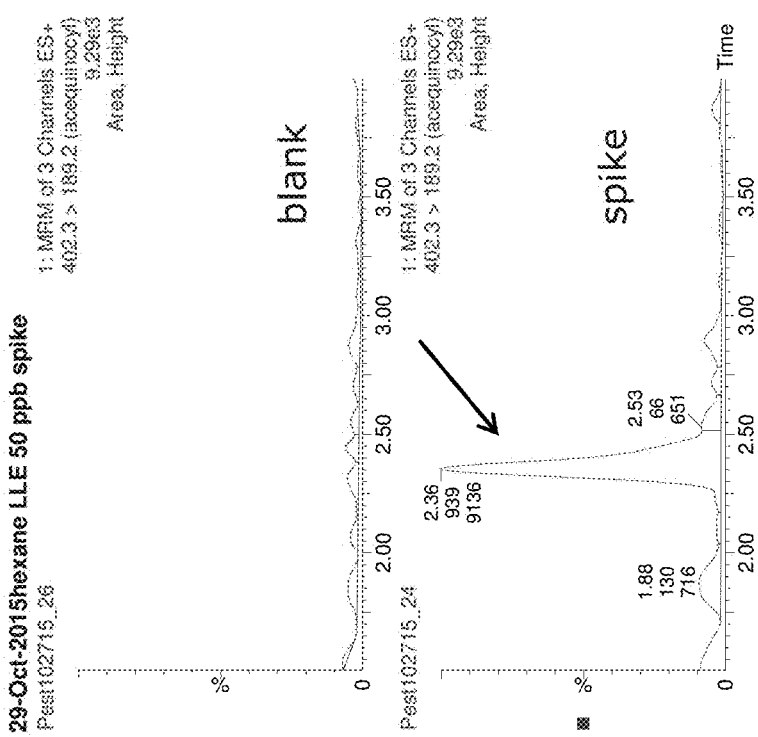
FIG. 4 is a panel showing mass spectra of the MRM transitions 402→343 and 402→189 for a cannabis sample processed according to the methods of the invention and spiked with acequinocyl at 50 ppb.
Figure 4:
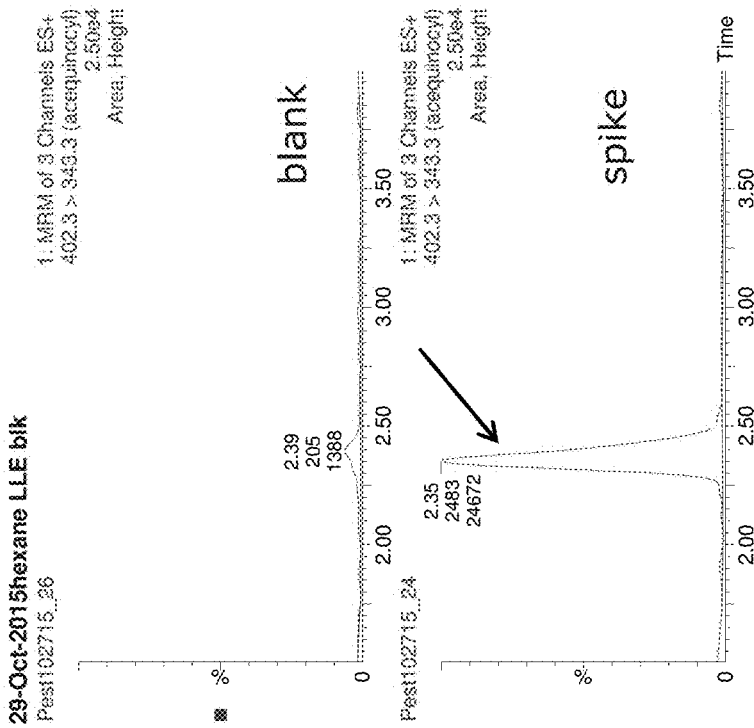

FIG. 4 is a panel showing mass spectra of the MRM transitions 402→343 and 402→189 obtained using a cannabis sample processed using methods of the invention and spiked with 50 ppb acequinocyl. FIG. 4 illustrates that the MRM transitions 402→343 and 402→189 can be used for quantifying acequinocyl, with the limit of quantification of about 10 ppb.

What is claimed is:

1. A method for detecting and quantifying a non-polar analyte in a plant-derived sample, comprising:
    (a) purifying said sample in a first purification step to obtain a first solution;
    (b) purifying said first solution in a second purification step comprising extracting said first solution with liquid-liquid extraction (LLE) or solid phase extraction (SPE) using a non-polar solvent to obtain a second solution; and
    (c) subjecting said second solution to detection and quantitative analysis;
        wherein when LLE is used, said non-polar analyte is retained in a non-polar liquid phase, and said second solution is said non-polar liquid phase comprising said non-polar analyte; and
        wherein when SPE is used, said non-polar analyte is initially retained on a non-polar solid phase and is then eluted from said non-polar solid phase in a separate elution step, and said second solution is said eluate from said non-polar solid phase comprising said non-polar analyte.

2. The method of claim 1, wherein said method results in detection of said non-polar analyte at a detection limit that is equal to or lower than a threshold detection limit.

3. The method of claim 2, further comprising:
    (d) subjecting said second solution to an analysis by liquid chromatography (LC) followed by mass spectrometry (MS).

4. The method of claim 3, wherein said liquid chromatography is ultra high pressure liquid chromatography (UHPLC).

5. The method of claim 3, wherein a mobile phase for said liquid chromatography comprises ammonium acetate.

6. The method of claim 3, wherein said mass spectrometry is tandem mass spectrometry (LC/MS/MS).

7. The method of claim 1, wherein said non-polar solvent is selected from the group consisting of pentane, hexane, cyclohexane, benzene, toluene, chloroform, diethyl ether and 1,4-dioxane.

8. The method of claim 7, wherein said non-polar solvent is hexane.

9. The method of claim 1, wherein said first purification step comprises extraction with a solution comprising acetonitrile and at least one salt.

10. The method of claim 9, wherein said salt is selected from the group consisting of sodium chloride, magnesium sulfate, trisodium citrate dehydrate and disodium hydrogen citrate sesquihydrate.

11. The method of claim 1, wherein said plant-derived sample comprises hops or cannabis.

12. The method of claim 11, wherein said non-polar analyte is acequinocyl, an acequinocyl derivative or a combination thereof.

13. The method of claim 12, wherein said acequinocyl derivative is acequinocyl-OH.

14. The method of claim 2, wherein said threshold detection limit is 1000 ppb or less.

15. The method of claim 1, wherein the non-polar analyte is acenoquinocyl, an acequinocyl derivative or a combination, the plant-derived sample comprises cannabis, and the non-polar liquid phase is hexane.

16. The method of claim 15, wherein said method results in detection of acequinocyl, an acequinocyl derivative or a combination thereof at a detection limit of 50 ppb or less.

17. The method of claim 6, wherein said LC/MS/MS comprises multiple reaction monitoring (MRM) using an ion selected from the group consisting of an ion having an M/Z of $343^+$, $385^+$ or $402^+$.

18. The method of claim 1, wherein the first solution consists of a supernatant from the first purification step.

19. The method of claim 14, wherein said threshold detection limit is 100 ppb or less.

20. The method of claim 19, wherein said threshold detection limit is 10 ppb or less.

* * * * *